United States Patent [19]
Rickards

[11] Patent Number: 6,012,812
[45] Date of Patent: *Jan. 11, 2000

[54] INDUSTRIAL SAFETY ASSEMBLY

[75] Inventor: Tom Rickards, Miami Beach, Fla.

[73] Assignee: The Energy Corp., Miami, Fla.

[*] Notice: This patent is subject to a terminal disclaimer.

[21] Appl. No.: 08/965,557

[22] Filed: Nov. 6, 1997

Related U.S. Application Data

[63] Continuation-in-part of application No. 08/709,359, Sep. 6, 1996, Pat. No. 5,717,479.

[51] Int. Cl.[7] .................................................... G02C 1/00
[52] U.S. Cl. ............................................ 351/158; 455/343
[58] Field of Search ............................ 351/158, 41, 123; 455/343, 344, 347, 350, 351

[56] References Cited

U.S. PATENT DOCUMENTS

| | | |
|---|---|---|
| 3,807,526 | 4/1974 | Sygnator . |
| 4,353,364 | 10/1982 | Woods . |
| 4,972,491 | 11/1990 | Wilcox, Jr. . |
| 5,367,345 | 11/1994 | da Silva . |
| 5,396,563 | 3/1995 | Yoshimi . |
| 5,717,479 | 2/1998 | Rickards ................................. 351/158 |

*Primary Examiner*—Hung Xuan Dang
*Attorney, Agent, or Firm*—Malloy & Malloy, P.A.

[57] ABSTRACT

An industrial safety assembly to be worn on a worker head in an industrial setting, the assembly including a speaker assembly structured and disposed to audibly communicate an audio signal received by a receiver assembly to the wearer through a speaker head. The speaker head, which is structured to be inserted into one of the wearer's ears so that the audio signal is clearly audible to the wearer in a loud industrial environment, is flexibly and communicably secured to the receiver assembly so as to permit variable positioning of the speaker head in accordance with a location of the wearer's ears. Further included in the safety assembly are a pair of disposable protective ear inserts structured to be inserted into the wearer's ears so as to substantially muffle any exterior noise. The protective inserts are removably secured to the speaker assembly such that each user can utilize their own clean pair. As such, a first of the protective inserts includes a bore formed therein and structured to receive the speaker head snugly, yet removably therein so that the audio signal is clearly audible to the wearer, the exterior noise is substantially muffled, and the speaker head is shielded from contact with the wearer and from perspiration or other body contaminants of the wearer.

20 Claims, 3 Drawing Sheets

INDUSTRIAL SAFETY ASSEMBLY

The present is a Continuation-in-Part to U.S. patent application Ser. No. 08/709,359 filed on Sep. 6, 1996 now U.S. Pat. No. 5,717,479.

BACKGROUND OF THE INVENTION

1. Field of the Invention

The present invention relates to an industrial safety assembly including eye protection, disposable, hygienic hearing protection, and a means for audibly receiving signals or sounds in a single, compact assembly that enables a worker in an industrial setting to maintain maximum safety and sanitary conditions while increasing productivity through communicability.

2. Description of the Related Art

In many industrial, mining, or construction related applications, employees are generally required to wear various types of protective gear, such as boots, hard hats, or gloves. Still, however, possibly the most important parts of the body to be protected are the eyes and ears of a worker. In particular, most industrial settings are quite loud such that prolonged exposure to the noise can result in permanent hearing loss. Also, because of the risk of small particles or potentially corrosive fluids being emitted from heavy machinery, a worker's vision can be at great risk if not properly protected. To this end, worker's are commonly required to wear some form of eye protection and/or hearing protection. Indeed, the need for eye and hearing protection frequently go hand-in-hand such that workers will often carry some form of safety goggles in addition to some form of ear coverings or plugs.

Often, the vision and hearing safety equipment is issued to a worker by the company in the form of a pair of protective glasses and a pair of disposable ear plugs. With regard to the ear plugs, although larger, exterior ear coverings which completely encase the ears are available, small, disposable plugs or devices containing plugs are highly preferred. In particular, the small ear plugs are less bulky, and therefore more comfortable, and are much more sanitary as each individual has their own plugs which are discarded after use. Further, the small ear plugs are much less expensive than the larger external ear covers. As such, if a company does choose to utilize external ear covers it will usually collect them at the end of a shift, and re-issue them immediately to another worker on the next shift, a practice which is not favorable as perspiration and contaminants from a previous user make the previously used external covers uncomfortable to wear and highly un-hygienic as the contaminants may easily be transferred from one worker to the next. As a result, whether to keep employees happy or to meet health guidelines, a business that chooses to use external ear coverings must often have an set of external ear covers available for every employee, an added expense that further dissuades the use of the external covers.

In addition to hearing and vision protection, another important safety consideration at an industrial work sight is communicability. Generally, workers carry a radio, or have some form of communication, such as a computer or a telephone near their work station. Unfortunately, however, workers can become quite isolated in the working environment, as their hearing protection blocks out all exterior noise including the phone or radio. Still, in an emergency it is very important that all of the workers communicate with one another so as to properly alert one another of dangers or shut downs, and so as to be aware of evacuations or other safety related notices.

Safety, however, is not the only reason businesses require communicability with their workers. Businesses also desire communicability to increase worker efficiency and productivity. In particular, if a worker is not informed, and/or cannot inform others of line shut downs, supply deliveries, and many other circumstances, a great deal of money can be lost in down time or defective production. For those reasons it is often vital that a worker be in communication with other workers at all times.

Presently in the art, businesses address the various safety and communicability considerations by issuing their employees separate radios, protective glasses, and ear plugs. Alternatively, some facilities attempt to use a computer work station monitor to provide worker's with a visual signal that they are being communicated with. Still, however, communication is a great inconvenience as workers must often remove their hearing protection to properly communicate. Further, even though some external head phone type ear covers, which provide for some communicability, are available, due to the previously described, expense, inconveniences and un-hygienic conditions associated with their use, those types of devices are not favored in the art and businesses must look to any available alternatives.

Accordingly, safety glasses, hearing protection, and communication devices are still commonly provided to workers separately, and the worker is called upon to manage all of the separate, and often incompatible devices as well as possible. Unfortunately, users who are able to simultaneously wear two or three separate devises find the combined use of the often incompatible apparatuses very inconvenient, bulky, and awkward for use on a day to day basis. Further, to ensure that a worker does not forget or misplace the often expensive equipment, in many instances some or all of the safety equipment, and especially the more expensive equipment such as the communication equipment and exterior head phone type covers, must be turned in each day and reissued the following morning. This practice frequently results in safety glasses, microphones, transmitters, and ear covers being lost, misplaced, or damaged during storage, as the use of several separate devices does not allow for easy convenient storage in one central location. As such, it is very difficult to keep track of all of the various types of safety equipment and a user still has no assurance that they are using all of their own equipment from day to day, a circumstance that is not only un-sanitary, but also can be quite inconvenient to a user who may have to re-size or otherwise adapt their equipment to their comfort requirements.

In the past, others in the arts relating to communication have attempted to provide devices which can transmit audible signals, while dampening exterior noise. These devices, however, tend to be adapted for a single user, and are quite expensive, making them ineffective for an industrial use wherein every worker is protected. For example, the patent to Woods (U.S. Pat. No. 4,353,364) discloses an ear acoustical attenuating device including a spiral type insert portion or a custom molded ear insert. Similarly, the patent to Wilcox, Jr. (U.S. Pat. No. 4,972,491) discloses an ear-mic headset which contains interior earplugs that fit into a user's ears. Such devices, however, are generally complex, are not suited for a multiple user situation wherein the same device must be shared, and are not cost effective to provide to each individual worker. Also, in the communication field, earphones such as the one provided in the patent to Yoshimi (U.S. Pat. No. 5,396,563) which include an elastic vibration generator/excitor coupled with a sound insulating plug that is structured to propagate the elastic wave therethrough. This device, which has as a primary application the race car industry, does not disclose or suggest efficient, sanitary multi-person use, as the sound transmitting portion, namely the elastic wave propagating plug coupled with the excitor, is to be inserted completely into a user's ear cavity such that all of it may become subject to perspiration or contamination. Indeed, such a device requires secure and precise configuration so as to ensure that the waves are effectively propagated through the plug, and as such does not provide for any disposability. Also, despite the generally loud race car environment, industrial environments can often be much louder with may more varied exterior noises such that a device such as Yoshimi's can tend to be muffle the audio signal and may not provide sufficient clarity to contrast a large variety of exterior noises. Further, none of these communication devices truly address all of the safety needs in an industrial setting by providing a single, ergonomically oriented, sanitary multi-user safety device.

Similarly, other devices in the past, such as the audio eyeglasses of da Silva (U.S. Pat. No. 5,367,345) and the ear protector of Sygnator (U.S. Pat. No. 3,807,526) have attempted to combine some devices. In particular, both of these devices seek to combine an ordinary eyeglass frame with a head phone or an ear plug. Unfortunately, however, such devices do not fully address an industrial wearer's safety needs, do not address the sanitary considerations associated with a multi-user environment, and are not adapted for comfortable use in a multi-user environment as they are not easily adaptable for a precise fit on user's of different sizes. Specifically, most devices in the art relating to communication devices do not have to be structured around other types of protective equipment and can therefore be secured as part of an over the head mount which can be easily adjusted to a wearer's size without concern as to the position of the overhead mount so long as it supports the assembly.

Accordingly, there is still a need in the specialized art relating to industrial safety equipment for a safety unit which will ensure that worker always has all of the necessary safety devices in a convenient to use array that may be easily and efficiently labeled and re-distributed to assigned employees, thus reducing waste, loss and inconvenience. Further, there is a need for a safety unit which ensures that a user is wearing all of the necessary hearing, vision and communication safety devices and which enables workers in a multi-user/multi-shift environment to effectively and safely share or pass on the safety unit as it is structured to provide quick and precise fitting on user's of varying sizes, complete safety protection and maximum hygiene from user to user as all reusable portions are concealed from direct contact with a wearer. Additionally there is a significant need for a device which combines hearing protection and communication in a manner which has sanitary, multi-use capabilities and provides clear, precise and focused reception of an audio signal to a user, even in a very loud environment with multiple varying sounds which can tend to muffle or otherwise disrupt audio perception.

SUMMARY OF THE INVENTION

The present invention is directed towards an improved, multi-user, industrial safety assembly which preferably combines eye protection, hearing protection, and communicability into one lightweight, fully integrated, self-contained unit, but at least incorporates clear, precise communication with sanitary and effective hearing protection. The safety assembly includes a receiver assembly. The receiver assembly may be mounted to a frame assembly and is structured to receive an audio signal from a remote source. Connected with the receiver assembly, so as to audibly transmit the audio signal received by thereby, is at least one speaker assembly. The speaker assembly includes primarily a speaker head, which is structured to be inserted into one of the wearer's ears, such that the audio signal can be heard in a loud industrial environment and such that the audio signal is emitted in a focused and clear manner directly into the user's auditory canal. The speaker head is preferably flexibly and communicably secured to the receiver assembly by a generally elongate, flexible speaker connection. The speaker connection is structured and disposed to variably position the speaker head relative to the receiver assembly in accordance with a location of the user's ears, thereby providing for a precise fit despite a specific position of the user's ear relative to the receiver assembly.

The safety assembly further includes at least one, but preferably a pair of disposable, protective ear inserts which are structured to be inserted into the user's ears in order to substantially muffle any exterior noise. At least a first of the protective ear inserts includes a bore extending axially therein and preferably completely or substantially therethrough. The bore is configured such that the speaker head is removably inserted therein and such that the audio signal is transmitted unabated through the protective ear insert directly to the user in a manner that is substantially clear and audible to the user while only the exterior noise is substantially muffled in the loud industrial environment. As such, the protective ear inserts can easily and inexpensively be removed and replaced to preserve maximum hygiene for a subsequent user without affecting the effectiveness thereof. Moreover, the protective ear insert is preferably structured to substantially shield the perimeter of the speaker head from contact with the user and from perspiration or other body contaminants of the user.

An object of the present invention is to provide an industrial safety assembly which combines communicability with effective hearing protection in a sanitary and multi-user fashion, and in a manner which provides a current user with a clear, highly audible audio signal without compromising the disposability, ease of use or hygenity of the assembly.

It is also an object of the present invention to provide a multi-user industrial safety assembly which combines eye protection, disposable hearing protection, and communication devices into one lightweight fully integrated self-contained unit.

It is a further object of the present invention to provide an industrial safety assembly which can be hygienically utilized by a number of wearers.

It is an additional object of the present invention to provide a moderate cost, self contained, safety assembly which facilitates and thereby ensures that a worker's vision and hearing are protected while they are still in safe communication with others.

Another object of the present invention is to provide an industrial safety assembly which is structured to provide multiple types of protection in an easily adaptable unit that may be effectively worn by different size users without requiring alteration or re-sizing.

An object of the present invention is to provide hearing protection with communicability in a non-cumbersome, well fitting unit which also provides complete front and side vision protection.

An additional object of the present invention is to provide a unique and comprehensive combination of need safety equipment into a single, ergonomically arranged assembly.

Another object of the present invention is to provide a comprehensive combination of need safety equipment such as vision and hearing protection into a single, ergonomically arranged assembly that is structured to enable partial removal of one aspect of safety protection, such as when a wearer wishes to wipe their eyes or brow, without removing other necessary safety features.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Shown throughout the figures, the present invention is directed towards a safety assembly generally indicated as 10. An embodiment of the safety assembly 10 is structured primarily to be worn on a workers head in a substantially loud industrial type environment wherein particulate or corrosive fluids may inadvertently affect a worker's eyes and wherein communicability with workers is a vital safety and productivity concern. The main types of safety equipment which are ergonomically combined into the single, easy to wear and use, self-contained safety assembly 10 relate to eye protection, hearing protection, and communicability, a comprehensive combination which solves a previously unaddressed, industry wide problem of workers not implementing all of the necessary safety equipment. Looking to the preferred embodiment of FIG. 6, the safety assembly 10' primarily provides an employer the ability to effectively and precisely communicate with its employees, while also ensuring the worker's hearing is effectively protected and not compromised by the need to communicate with them. Looking to the preferred embodiment of the safety assembly 10', it is structured to provide effective and properly fitting protection against hearing loss. As such, the safety assembly 10' includes at least one, but preferably a pair of protective ear inserts 61 and 62. The first and second protective ear inserts 61 and 62 are structured to substantially muffle very loud exterior sounds when inserted into the user's/wearer's ears. Preferably, the first and second ear inserts 61 and 62 are formed of a sound-deadening, compressible, and inexpensive material such as high density urethane form. As such, the protective inserts 61 and 62 are preferably disposable, thereby maintaining sanitary conditions and ensuring that each individual only inserts their own protective inserts 61 and 62 into their ears. Of course, inserts of varying materials and configurations could also be utilized, such as from solid, pre-molded or formed materials, such as silicone, and/or inserts having separate disposable, protective covers may be employed if desired.

Figure 6:
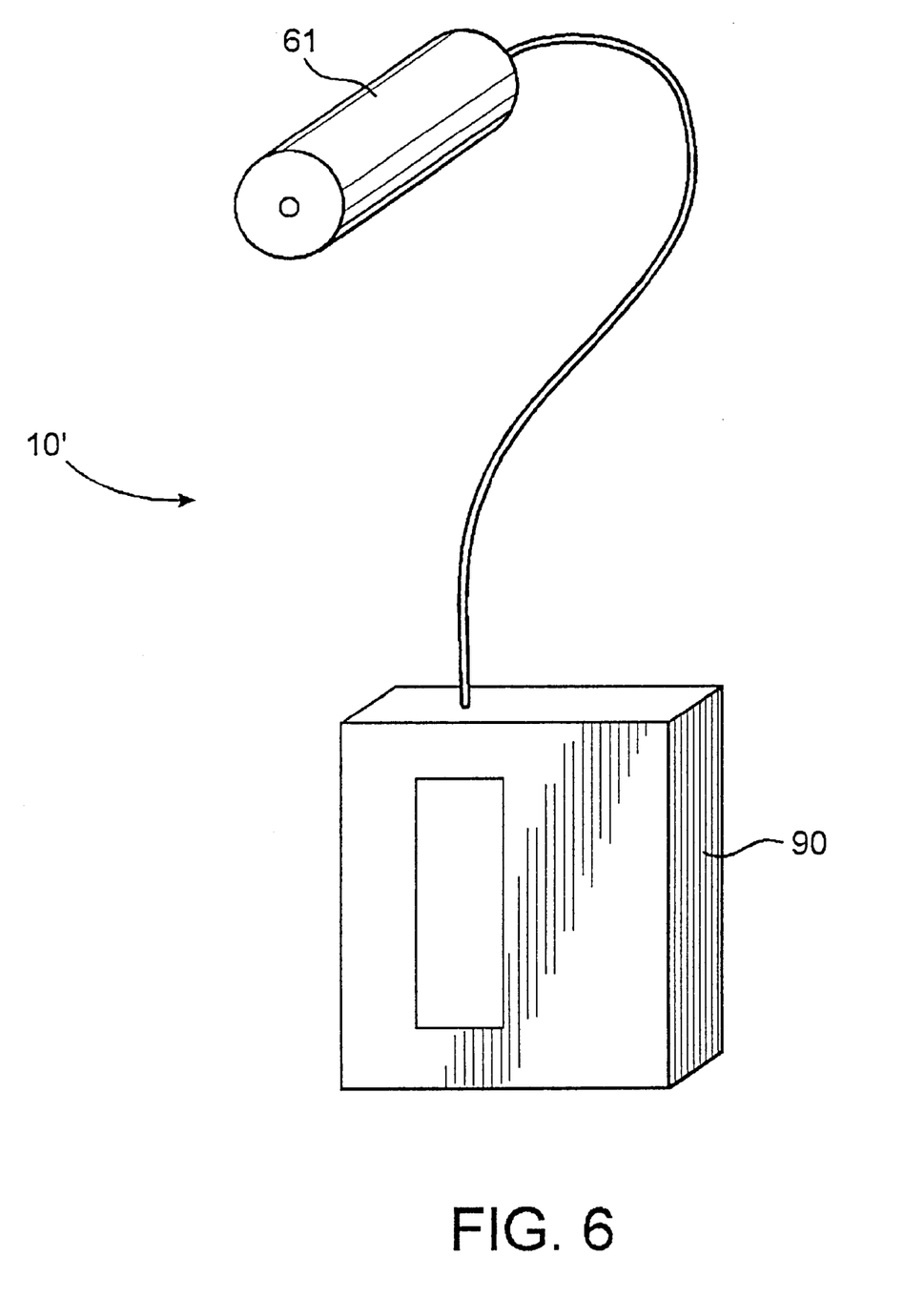
FIG. 6 is a perspective view of a preferred embodiment of the safety assembly of the present invention.

In addition to hearing protection, the safety assembly 10' of the present invention is also structured to provide substantial communicability between a wearer and other wearers or a control station. Accordingly, the safety assembly 10 further includes a receiver assembly 68. The receiver assembly 68 is structured to receive an audio signal from a remote location, and is preferably substantially small and compact so as to be easily carried by the user. Further, because the audio signal is received within an industrial setting, a generally large antenna is not required as the signals are usually transmitted from close by.

Connected with the receiver assembly 68 is a speaker assembly. The speaker assembly is structured and disposed to audibly communicate the audio signal to the wearer, and to this end, the speaker assembly includes a speaker head 63. The speaker head 63 is structured to be introduced into a wearer's ear such that the audio signal is substantially audible to the wearer in the loud industrial environment. In the preferred embodiment, the speaker head 63 is flexibly and communicably secured to the speaker assembly by a generally elongate, flexible speaker connection 64. The speaker connection 64 is structured and disposed to variably position the speaker head 63 relative to the receiver assembly in accordance with a location of the wearer's ears, thereby ensuring that the speaker head 63 is effectively positionable in the wearer's ear despite the location of the wearer's ear relative to the receiver assembly. Further, the flexible speaker connection 64 is generally elongate so as to permit the speaker head 63 to be maintained in the wearer's ears as the wearer moves around. In a preferred embodiment, the flexible speaker connection includes a generally hollow sound tube. As such, the receiver assembly 68 preferably includes an isolated internal speaker to which the sound tube is connected in order to transmit the sound therethrough to the speaker head 63, which in this embodiment includes a sound emitting opening. Alternatively, the flexible speaker connection 64 may include an elongate, sound transmitting wire which transmits the audio signal to the speaker head 63 which itself is structured to convert the audio signal into audible sound. Of course, with advancing technology, it is possible that the speaker head 63 be connected to the receiver assembly via wireless means.

In the preferred safety assembly 10' of the present invention, the flexible speaker connection 64 also defines one of preferably a pair of flexible insert connections which are structured to ensure an appropriate protective fit of the protective inserts 61 and 62, despite the precise size of the wearer, while also ensuring that the protective inserts 61 and 62 are maintained with the overall safety assembly 10' if the wearer temporarily removes it. In order to accommodate the flexible speaker connection 64, the first protective ear insert 61 is preferably structured to include a bore 61' which extends axially through the first protective insert 61. Preferably the bore 61' extends substantially or completely through the protective ear insert 61 and is structured to receive the speaker head 63 snugly, yet removably therein. Accordingly, once the speaker head 63 is inserted into the protective insert 61, and the protective insert 61 is inserted into the wearer's ear, the protective insert 61 substantially shields the speaker head 63 from contact with the wearer and from perspiration or other body contaminants of the wearer so as to preserve maximum hygenity for multiple users merely by providing for the removal of a particular user's used protective inserts 61 and 62. Moreover, the protective inserts 61 and 62 substantially muffle the loud exterior noise, while still permitting the audio signal to be heard and understood by the wearer in a clear and precise manner.

Specifically, because of the configuration of the present invention, the speaker head 63 extends into the wearer's ears and is not distorted or muffled in any way by the protective inserts themselves. As such, the audio signal is crisp and focused without disruption from loud and varied exterior noises. For example, an industrial environment often includes a large number of different noises which must be eliminated. These noises, however, are all at different volumes, pitches, rates, etc. and can make it very difficult to hear an audio signal with precision. By directing the audio signal into the wearer's ears as is achieved by the present invention, and only muffling those exterior noises, a great degree of precision and focus is achieved. Also, such focus can be of particular importance in an industrial environment wherein a wearer is not always expecting to hear an audio signal but rather has their attention spread over a variety of tasks.

Similarly to the first protective ear insert 61, the second ear insert 62 preferably includes a bore 62' which extends axially at least partway therethrough. As such, the protective inserts 61 and 62 can be identically manufactured and are interchangeable with one another. Although the second ear insert 62 can be completely un-connected, in the preferred embodiment, the flexible insert connection 66 are associated with the second protective ear insert 62 and include an elongate chord 66. In this embodiment, the elongate chord 66 is connected at one end thereof to the receiver assembly. Specifically, the flexible insert connection 66 includes a connector head structured to be removably, yet snugly inserted into the bore 62' in the second protective ear insert 62, the connector head possibly being constructed of a sound muffling material as an audio signal is not to be transmitted therethrough. As such, both the first and second protective ear inserts 61 and 62 may be effectively and easily introduced into the ears during use, with minimal risk of loss when removed and with maximum hygiene. Of course, if desired, both protective ear inserts 61 and 62 can receive a speaker assembly coupled therewith to provide a "stereo" type reception.

The alternative embodiment of the safety assembly 10, as illustrated in FIGS. 1–5, includes a frame assembly 15 which is to be worn on the wearer's head. In particular, the frame assembly 15 includes a front frame member 20, and some means to hold the frame assembly 15 on the wearer with the front frame member 20 in confronting relation to the user's eyes. In the illustrated embodiment, the frame assembly 15 further includes a first leg 21 and a second leg 22. The front frame member 20, which is preferably constructed of durable, lightweight plastic or a similar lightweight generally rigid material, preferably includes a pair of eye segments 23 and 24, although a unitary panel or shield type construction could be achieved. The eye segments 23 and 24 are structured and disposed to fit over each of the wearer's eyes and are connected with one another by a bridge segment 25. As with conventional glasses, the bridge segment 25 fits over the wearer's nose and functions to substantially supportably maintain the front frame member 20 thereon. Also, so as to provide comfort, a nose pad 30 constructed of soft, pliable material such as rubber or latex can be disposed in the bridge segment 25.

Figure 1:
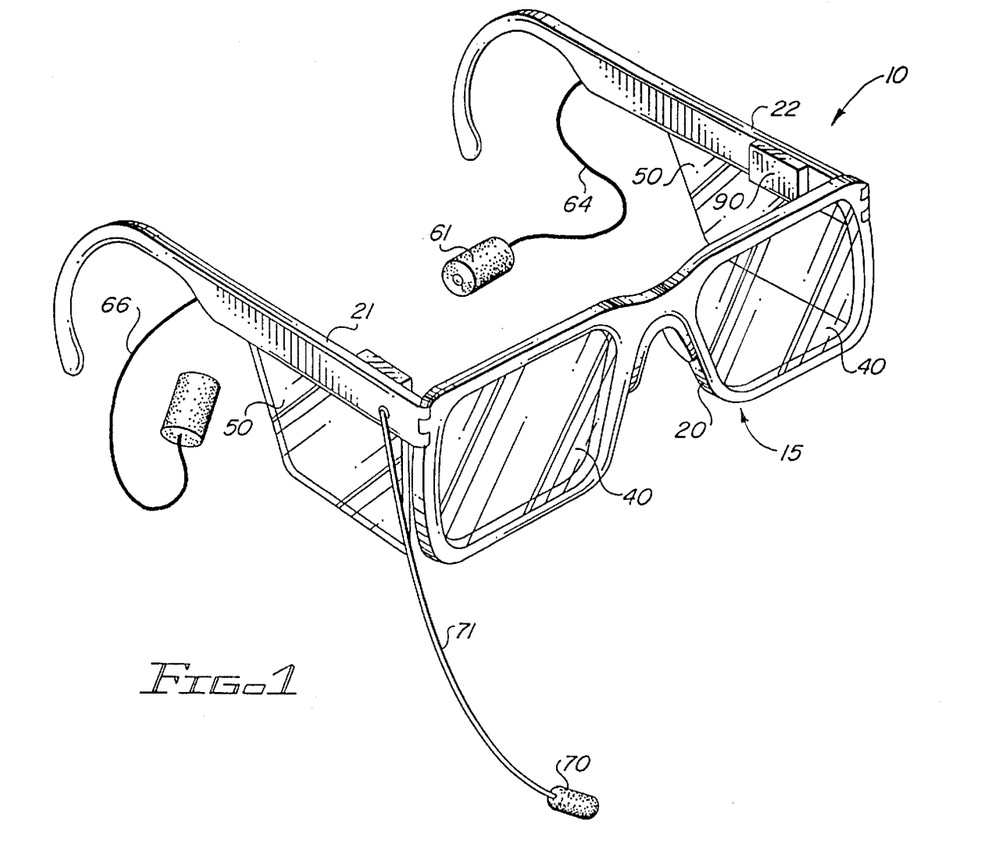
FIG. 1 is a perspective side view of an embodiment of the safety assembly of the present invention.
Figure 2:
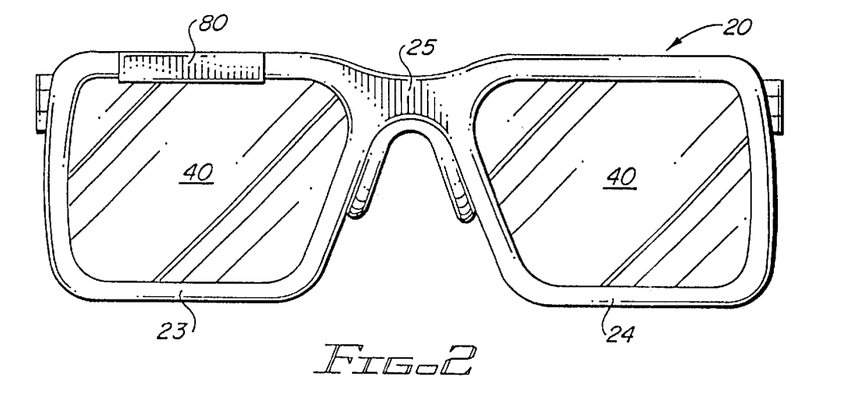
FIG. 2 is a view showing the front of the safety assembly of the present invention.
Figure 3:
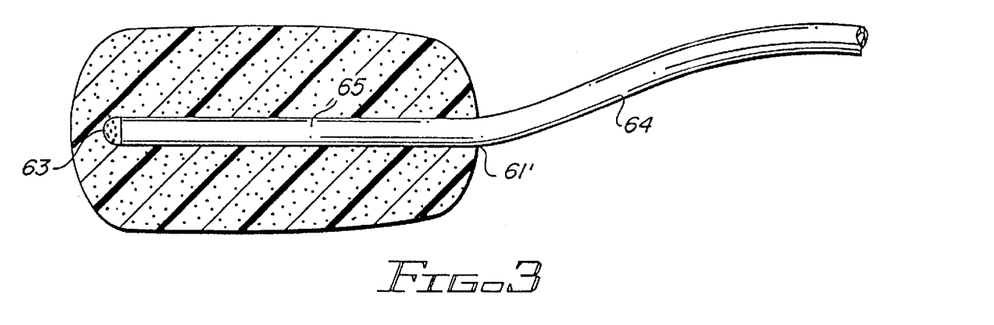
FIG. 3 is a sectional view of the first ear insert showing the speaker head and sound tube.
Figure 4:
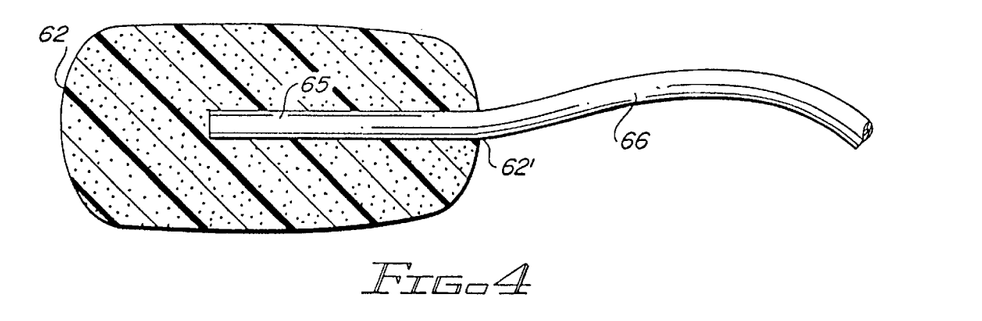
FIG. 4 is a sectional view of the second ear insert with the attachment cord.

Disposed in the front frame member 20 is at least one transparent, preferably shatterproof front eye panel 40. The front eye panel is structured and disposed to substantially shield the front of the wearer's eyes while permitting clear vision therethrough. Further, the eye panel 40 may include two separate panels, each disposed in one of the eye segments 23 and 24 of the front frame member 20 so as to cover/shield a corresponding eye of the wearer. Alternatively, however, the front eye panel 40 may include one continuous segments which extends across the bridge segment 25 into both eye segments 23 and 24, thereby functioning to shield the front of both of the wearer's eyes. Also, for industrial applications where bright lights are expected such as those produced by welding torches, the front eye panel 40 may be tinted or polarized. Of course, tinted panels may also be desirable for outdoor use in bright sunlight. Further, an individual worker may wish to replace the front eye panel 40 with prescription safety lenses.

Turning to the first and second legs 21 and 22, they are structured to extend from opposite sides of the front frame member 20 towards a rear thereof. Further, the legs 21 and 22 are preferably disposed in a generally perpendicular relation relative to the front frame member 20 so as to extend over the wearer's ears upon the front frame member 20 being disposed in front of the wearer's eyes. In the preferred embodiment, each of the legs 21 and 22 have a curved free end and are structured to curve over the wearer's ears so that the front frame member 20 is effectively retained and positioned in front of the wearer's eyes during activity by the worker. The first and second legs 21 and 22 may also be formed of a durable, lightweight plastic or in an alternative may be made of a resilient, bendable plastic material with a bendable metal core to allow the user to adjust the contour of the legs 21 and 22 to provide a precise comfortable fit.

In additional to the risk of particulate or contaminants entering a wearer's eyes from the front, many industrial eye injuries involve particles or contaminants entering the wearer's eyes from a side. In the preferred embodiment, the sides of the wearer's eyes are shielded by a pair of side eye panels 50. The side eye panels 50, which are preferably formed of transparent, shatter proof material so as to provide effective protection without limiting a peripheral vision of the wearer, are preferably secured to the first leg 21 and the second leg 22 of the frame assembly 15. Further, the side eye panels 50 are preferably gradually tapered back towards the wearer's ears in order to ensure full protection without impeding a comfortable fit over the wearer's ears. Although the side eye-panels are preferably permanently secured to the legs 21 and 22, such as by a pair of screws, is an alternative embodiment the side panels can be structured to "snap-on" so that they may be removed in instances where side eye protection is not needed.

In addition to eye protection, this embodiment of the safety assembly 10 of the present invention is also structured to provide effective and properly fitting protection against hearing loss. As such, the safety assembly 10 includes a pair of protective ear inserts 61 and 62. The first and second protective ear inserts 61 and 62 are structured to be maintained with the safety assembly 10 if the wearer temporarily removes it, by flexible insert connection means 64 and 66. The flexible insert connection means 64 and 66 are removably secured to each of the protective ear inserts 61 and 61, in a manner previously described, so as to permit the protective ear inserts 61 and 62 to be variably positionable relative to the frame assembly 15, in accordance with the location of the wearer's ears. Also, the elongate nature of the flexible insert connection means 64 and 66 permits the frame assembly 15 to be partially removed from a wearers face, such as if a wearer must wipe their eyes or brow, while not removing the protective ear inserts 61 and 62 and subjecting the wearer to loud noises. In the preferred embodiment, the flexible insert connection means 64 and 66 preferably extend from the first and second legs 21 and 22, however they can also be effectively secured to the front frame member 20 if necessary by extending a length of the connection means 64 and 66.

Figure 5:
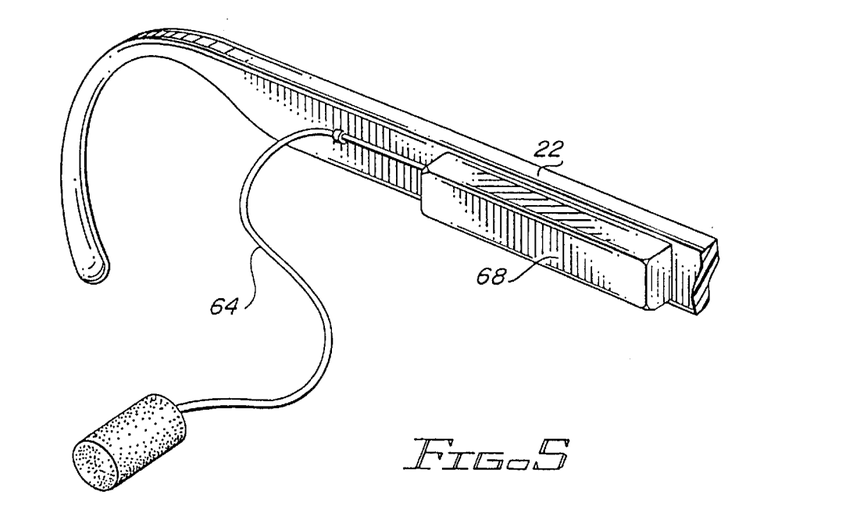
FIG. 5 is a sectional perspective view of an embodiment of the receiver assembly disposed on the frame assembly.

In addition to hearing and vision protection, this embodiment of the safety assembly 10 of the present invention is also structured to provide substantial communicability between a wearer and other wearers or a control station. Accordingly, the safety assembly 10 further includes the previously described receiver assembly 68 and corresponding speaker assembly. In this embodiment, the receiver assembly 68 is mounted to an inside surface of the second leg 22, preferably near the front frame member 20, as that area of the leg 22 is generally spaced from the wearer due to a normal configuration of the frame assembly 15. Additionally, to allow hands-free communication, the receiver assembly 68 of either embodiment of the present invention may be structured to include a transmitter assembly as well, either as a separate component or as part of a combined transmitter/receiver. Specifically, the transmitter assembly is structured to transmit an outbound audio signal initiated by the wearer to a remote location. As such, in this embodiment a microphone assembly 70 is also included. The microphone assembly 70 may be structured to be positionable within the vicinity of the wearers mouth by means of an adjustable elongate segment 71. Preferably the elongate segment 71 extends from the second leg 22 of the main assembly. Further, the elongate segment 71 may be constructed of a bendable, resilient plastic material which contains a light metal core so that the elongate segment 71 is adjustable to comfortably remain in front of the users mouth. As such the microphone assembly 70 allows for communication by the user while keeping his hands free to simultaneously work on other tasks.

In yet another embodiment, a heads up display transmitter 80 will be affixed to the front frame member 20 (As shown on FIG. 2). The heads up display transmitter is structured to provide a visual image on the eye panel 40 in front of the wearers eyes that appears to be a visible distance away from the wearer. This allows the wearer to view visual images such as machinery gauge readings and safety alerts without having to look away from his immediate task. Such a heads up display is very valuable in industrial applications where a short lapse of attention or a break in concentration may lead to mistakes or accidents.

The heads up display transmitter 80, as well as the receiver/transmitter assembly 68 will preferably receive power from a battery pack 90. Preferably, the battery pack, which can be rechargeable, can be mounted to the first leg 21 in an out of the way location.

While this invention has been shown and described in what is considered to be a practical and preferred embodiment, it is recognized that departures may be made within the spirit and scope of this invention which should, therefore, not be limited except as set forth in the claims which follow and within the doctrine of equivalents.

Now that the invention has been described,
What is claimed is:

1. An improved industrial safety assembly comprising:
   a receiver assembly structured and disposed to receive an audio signal,
   at least one speaker assembly, said speaker assembly being structured and disposed to audibly communicate said audio signal received by said receiver assembly,
   said at least one speaker assembly including a speaker head structured to be inserted into one of the wearer's ears such that said audio signal is substantially audible to a user in a loud industrial environment,
   at least one disposable protective ear insert structured and disposed to be inserted into the user's ears so as to substantially muffle exterior noise,
   said protective ear insert including a bore disposed axially therein from a first face thereof; and
   said bore in said protective ear insert being structured and disposed to receive said speaker head removably therein such that said audio signal is substantially audible to the user directly from said speaker head and the exterior noise is substantially muffled in the loud industrial environment.

2. An improved industrial safety assembly as recited in claim 1 wherein said protective ear insert are structured to substantially shield said speaker head from contact with the user and from perspiration or other body contaminants of the user.

3. An improved industrial safety assembly as recited in claim 1 wherein said speaker head is flexibly and communicably secured to said speaker assembly by a generally elongate, flexible speaker connection structured and disposed to variably position said speaker head in accordance with a location of the user's ears.

4. An improved industrial safety assembly as recited in claim 3 wherein said speaker head audibly generates said audio signal.

5. An improved industrial safety assembly as recited in claim 3 wherein said flexible speaker connection includes an elongate sound tube connected at a one end with an internal speaker of said receiver assembly, and connected at an opposite ends with said speaker head, said speaker head including a sound transmitting opening therein.

6. An improved industrial safety assembly as recited in claim 1 wherein said bore extends completely through said protective ear insert.

7. An improved industrial safety assembly as recited in claim 1 further including a frame assembly structured to be worn by a user.

8. An improved industrial safety assembly as recited in claim 7 wherein said frame assembly is structured to be supportably disposed on a head of the user.

9. An improved industrial safety assembly as recited in claim 8 wherein said frame assembly further includes at least one substantially transparent, substantially shatter proof material eye panel disposed so as to shield the wearer's eyes.

10. An improved industrial safety assembly as recited in claim 8 further including two of said protective ear inserts.

11. An improved industrial safety assembly as recited in claim 10 wherein said protective ear inserts are coupled to said frame assembly such that said protective ear inserts are variably positionable relative to said frame assembly in accordance with the location of the user's ears.

12. An improved industrial safety assembly as recited in claim 11 wherein said first of said protective ear inserts is coupled to said frame assembly by said speaker assembly, and a second of said protective ear inserts is coupled to said frame assembly by an insert connection assembly.

13. An improved, industrial safety assembly as recited in claim 12 wherein said insert connection includes an elongate cord having said connector head secured to a free end thereof, said connector head having a generally increased diameter relative to said cord and being structured to be fitted into said bore in said second ear insert so as to firmly, yet removably maintain said second ear insert connected to said frame assembly.

14. An improved industrial safety assembly as recited in claim 8 wherein said speaker assembly is coupled to said frame assembly.

15. An improved industrial safety assembly as recited in claim 14 wherein said speaker head is flexibly and communicably secured to said speaker assembly by a generally elongate, flexible speaker connection structured and disposed to variably position said speaker head relative to said frame assembly in accordance with a location of the user's ears.

16. An improved industrial safety assembly as recited in claim 8 further including two of said protective ear inserts, a first of said protective ear inserts being coupled to said frame assembly by a flexible speaker connection assembly.

17. An improved industrial safety assembly as recited in claim 8 wherein said receiver assembly is coupled to said frame assembly.

18. An improved industrial safety assembly as recited in claim 1 wherein said receiver assembly further includes transmitter assembly structured and disposed to transmit an outbound audio signal.

19. An improved industrial safety assembly as recited in claim 18 wherein said transmitter assembly includes a microphone assembly structured and disposed to pick up said outbound audio signal from the used.

20. An improved, industrial safety assembly as recited in claim 1 further including a power supply structured to provide power to at least said receiver assembly.

* * * * *

UNITED STATES PATENT AND TRADEMARK OFFICE
CERTIFICATE OF CORRECTION

PATENT NO.    : 6,012,812
DATED         : January 11, 2000
INVENTOR(S)   : Tom Rickards It is certified that error appears in the above-identified patent and that said Letters Patent is hereby corrected as shown below:

<u>Title page, Item [54] and Column 1, line 1,</u>
Title should read -- AN INDUSTRIAL HEARING PROTECTION AND COMMUNICATION DEVICE --

Signed and Sealed this

Twenty-first Day of October, 2003

JAMES E. ROGAN
*Director of the United States Patent and Trademark Office*